(12) United States Patent
Schuller

(10) Patent No.: US 7,774,071 B2
(45) Date of Patent: Aug. 10, 2010

(54) IMPLANTABLE CONDUCTING LEAD

(75) Inventor: Peter Schuller, Turramurra (AU)

(73) Assignee: Cochlear Limited, Lane Cove, NSW (AU)

( * ) Notice: Subject to any disclaimer, the term of this patent is extended or adjusted under 35 U.S.C. 154(b) by 399 days.

(21) Appl. No.: 10/531,716

(22) PCT Filed: Oct. 16, 2003

(86) PCT No.: PCT/AU03/01369

§ 371 (c)(1),
(2), (4) Date: Sep. 9, 2005

(87) PCT Pub. No.: WO2004/035133

PCT Pub. Date: Apr. 29, 2004

(65) Prior Publication Data

US 2006/0206185 A1    Sep. 14, 2006

(30) Foreign Application Priority Data

Oct. 17, 2002   (AU)  ............................. 2002952146

(51) Int. Cl.
*A61N 1/05* (2006.01)
(52) U.S. Cl. ................... 607/116; 607/119; 607/137
(58) Field of Classification Search ......... 607/115–116, 607/119, 122
See application file for complete search history.

(56) References Cited

U.S. PATENT DOCUMENTS

| | | | | |
|---|---|---|---|---|
| 4,573,481 A | * | 3/1986 | Bullara | 607/118 |
| 5,824,026 A | * | 10/1998 | Diaz | 607/116 |
| 7,149,585 B2 | * | 12/2006 | Wessman et al. | 607/116 |

FOREIGN PATENT DOCUMENTS

| | | |
|---|---|---|
| CA | 1146228 A | 5/1983 |
| EP | 1050269 A | 11/2000 |
| WO | WO 83/04182 A | 12/1983 |
| WO | WO 02/089907 A | 11/2002 |

* cited by examiner

*Primary Examiner*—George R Evanisko
*Assistant Examiner*—Rex Holmes
(74) *Attorney, Agent, or Firm*—Connolly Bove Lodge & Hutz LLP

(57) ABSTRACT

An electrically conducting lead (20) that can used in the body for electrical stimulations applications, such as a cochlear implant. The lead comprises a body of relatively electrically insulative material (41) having a relatively electrically conductive element (18) extending therethrough in a wound arrangement. The electrically conductive element (18) is comprised of a plurality of layers of electrical conductors (14). The conductive element (18) is disposed in the lead such that the longitudinal extent of each of the electrical conductors (14) is the same.

14 Claims, 12 Drawing Sheets

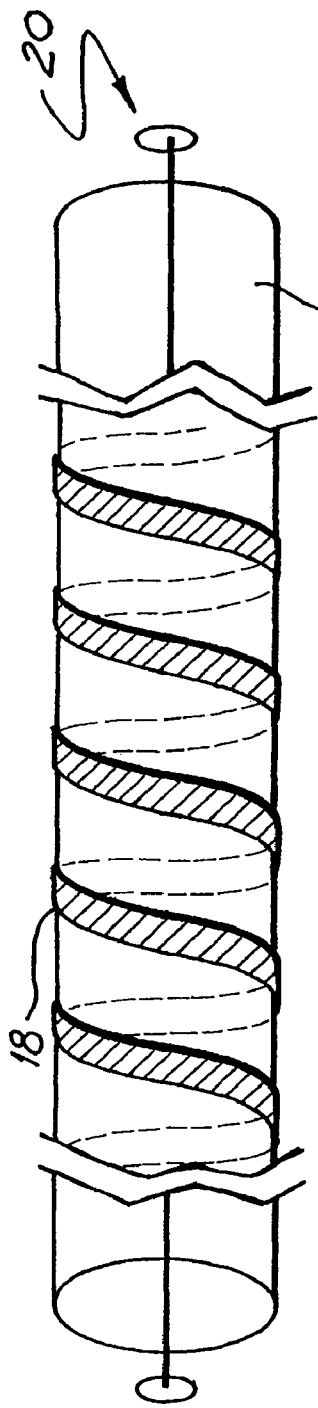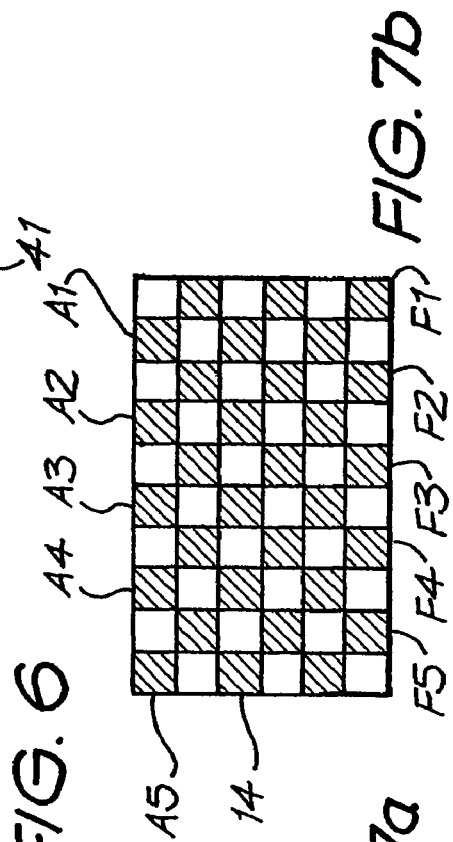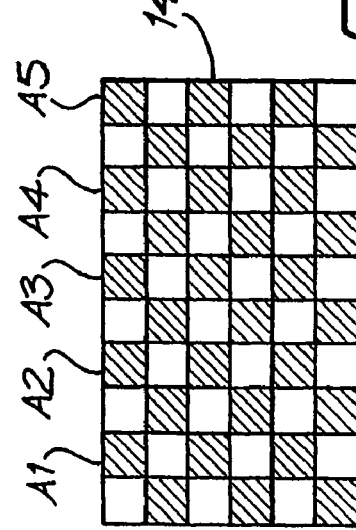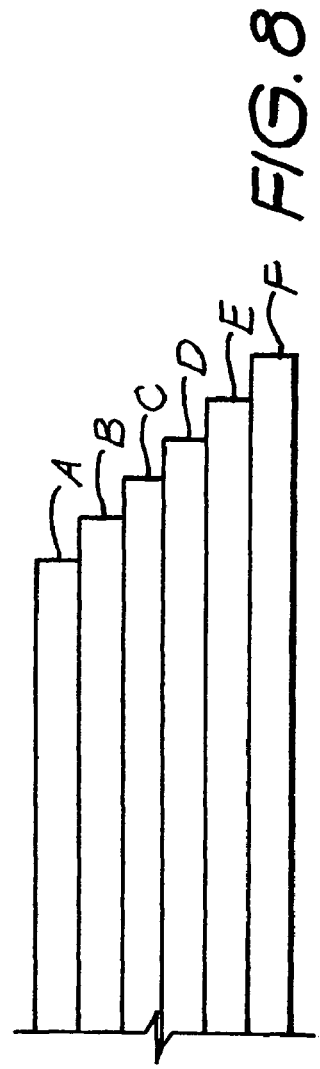

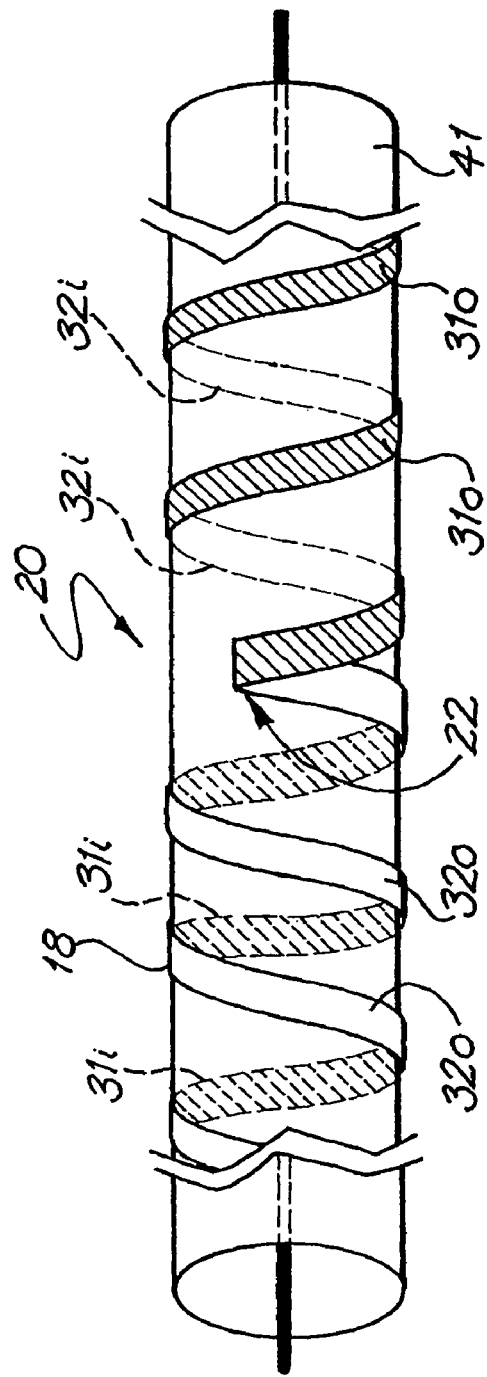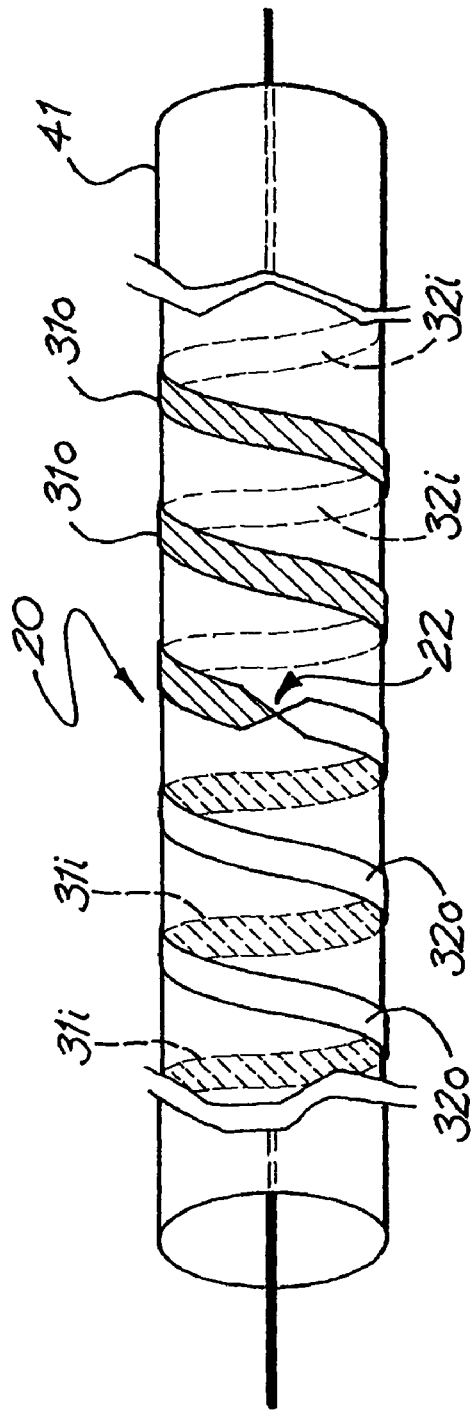
FIG. 9
FIG. 10

IMPLANTABLE CONDUCTING LEAD

CROSS-REFERENCE TO RELATED APPLICATIONS

This application claims the priority of and is a national stage application of PCT Application No. PCT/AU2003/001369, entitled, "Implantable Conducting Lead," filed on Oct. 16, 2003, which claims the priority of Australian Patent No. 2002952146, filed on Oct. 17, 2002. The entire disclosure and contents of the above applications are hereby incorporated by reference.

TECHNICAL FIELD

The present invention relates to an electrically conducting lead suitable for use with an implantable medical device. More particularly, the present invention relates to an implantable conducting lead having a layered conducting element with multiple conducting portions.

BACKGROUND OF THE INVENTION

Medical devices capable of being implanted in the body to provide therapy to a recipient have become increasingly common over recent times. Devices such as pacemakers, defibrillators, cochlear implants and functional electrical stimulation systems have all proven successful in providing useful therapy to recipients across a broad spectrum of applications.

Fundamental to all such devices is the provision of an implantable stimulator unit fixedly implanted within the body of the recipient. This stimulator unit is typically capable of receiving control signals from a device external to the recipient via a transcutaneous link. As well as control signals, the implanted stimulator unit may also receive power from an external device via the same or an alternative transcutaneous link.

Upon receipt of control signals and/or power, the stimulator unit typically then directs and controls the stimulation to be applied by the system. In the case of cochlear implants, the stimulator system may select the desired electrode and send a stimulation pulse to the electrode having a desired amplitude and pulse width. Typically, the stimulator unit is provided with dedicated electronics which enable it to decode the received control signals and control the flow of stimulation current from the stimulator unit to the desired stimulation site.

With advancement in battery technology, it is becoming increasingly popular for implanted stimulator units to be provided with their own power source, usually in the form of a rechargeable battery, to provide operating power to the electronics of the stimulator unit. In this regard, such devices can operate, at least for a period of time without the need for any external devices. This is important for pacemaker devices as they do not need to rely upon a constant link with an external device to remain operational, and can continue to perform their important function by relying on their own power source. For devices such as cochlear implants, there is an increasing desire for such devices to operate invisibly without the need for external devices and for this reason the use of an implantable stimulator unit with its own power source is becoming increasingly desirable.

Apart from the implanted stimulator unit which houses the electronic circuitry and power source necessary to control the therapy applied by the implantable device, a means for actually applying the therapy is also fundamental to such systems. In most cases, the means for applying the therapy is typically one or more electrodes, strategically positioned close to the desired stimulation site, for applying the electrical stimulation to that particular site.

The stimulating electrodes are typically positioned remote from the implanted stimulator unit. For example, in cochlear implant applications the stimulator unit is typically positioned in a recess in the skull whilst the electrodes are implanted in the cochlea close to the desired nerves. In this regard, a lead connecting the electrodes and the stimulator unit is required, and such leads need to be designed in a manner to ensure that the electrical stimulation is delivered safely to the appropriate electrodes and that the link between the stimulating electrodes and the stimulator unit is sturdy and reliable.

Traditionally, the common way of providing this electrical connection between the stimulator unit and the electrodes has been via conducting wires within the lead. Such wires typically communicate with the electronics within the stimulator unit via a hermetic feedthrough device and are welded to the terminating electrodes thereby forming a conductive path from the stimulator unit to the electrodes along which the stimulation current can flow. Typically, the lead is insulated from the surrounding tissue via a coating of insulative material, such as silicone.

In providing such an implantable connecting lead, it is important that the lead is capable of a degree of flexibility to compensate for any movement between the implantable stimulator and the electrodes, such as movement which may naturally occur due to body growth. Without such flexibility, excessive force can be experienced in the lead, particularly at the connection points such as at the feedthrough, resulting in the lead failing to act as a conductor. Further to this, providing a flexible rather than a rigid connection between the electrodes and the stimulator unit provides for easier surgical placement of the electrodes close to the desired stimulation site, which ensures that the surgical procedure is simpler and requires less surgical skill.

The typical method of providing a lead capable of a degree of flexibility is to dispose the wires, either individually or as a group, in a helical arrangement along the length of the lead. The wires can then be enclosed in a coating of body-compatible polyurethane, or a suitable nonconductive plastic which has a requisite degree of flexibility. In this way, the lead can experience a degree of elongation without placing undue stress on the wires or at the point where the wires connect to the stimulator unit. Examples of such leads are described in U.S. Pat. No. 4,835,853 and International Patent Application Publication No WO 83/04182.

One problem with such prior art methods is that it is difficult to sort the wires in a manner that makes it easily identifiable which electrode they are connected to. As such, following the formation of the lead, it is a time consuming process to individually test each wire and identify which electrode it is connected to and to then ensure that this wire is connected to the stimulator unit in the appropriate manner. This problem is further exacerbated when the number of stimulating electrodes increases and hence the number of wires increases, such as in cochlear implants where the number of electrodes can be greater than 22.

The present applicant has developed a new process for manufacturing electrodes and conductors that connect the electrodes to a stimulator/control unit. This process and the resulting products are described in detail in International Patent Application No. PCT/AU02/00575, the contents of which are incorporated herein by reference. In essence, this process results in the formation of an electrode array comprising of a stack of offset electrodes, layered on top of each other. Each of the electrodes has a respective conducting portion extending from the electrode, with the conducting portion and the electrode being integral and constructed from one piece of material. In this regard, a connecting lead is provided consisting of a plurality of layered, parallel conducting portions extending in a longitudinal direction. Such a lead therefore resembles a layered ribbon conductor, considerably different from conventional wire leads.

With such a change in the traditional structure of conventional wire conductors used in implantable devices, there is a need to provide a conducting lead that is capable of maintaining the conductors in a flexible and insulative environment. Further to this, there is a need to provide a conducting lead that can take advantage of the ordered structure of layered conducting wires so that the conductors can be easily sorted and connected to the appropriate stimulator.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present invention is an electrically conducting lead comprising:
a body of relatively electrically insulative material; and
a relatively electrically conductive element extending through at least a portion of said insulative body in a helically wound arrangement;
wherein said electrically conductive element comprises a plurality of layers of electrical conductors, with each layer of electrical conductors being made up of a plurality of separate electrical conductors, with the position of each electrical conductor being constant with regard to its neighbour and the position of each layer of electrical conductors being constant with regard to its neighbouring layer over the length of said portion of said insulative body.

In a further embodiment of this aspect, the electrically conductive element extends from a first end to a second end of the lead.

According to a second aspect, the present invention is an electrically conducting lead comprising:
a body of relatively electrically insulative material; and
a relatively electrically conductive element extending through at least a portion of said insulative body in a wound arrangement;
wherein said electrically conductive element comprises a plurality of layers of electrical conductors with the longitudinal extent of each of said electrical conductor over said portion of the lead being substantially identical.

In this aspect, the wound arrangement of the electrically conductive element is preferably a helically wound arrangement. In this regard, the spacing or pitch of the wound arrangement can vary or be identical along said arrangement.

In a further embodiment of this aspect, the electrically conductive element extends from a first end to a second end of the lead. In this embodiment, the longitudinal extent of each of said electrical conductors over the length of the lead from the first end to the second end is substantially identical. More preferably, the longitudinal extent of the electrical conductors is identical.

In one embodiment, the electrically conductive element extending through said portion of the insulative body is wound in an anticlockwise direction and then in a clockwise direction if looking at the lead from the first end of the lead. It will be understood that if one was to look at the lead from the second end, the anticlockwise turns would appear to be turning clockwise and the clockwise turns anticlockwise. Still further, it will be appreciated that the electrically conductive element could be wound in a clockwise direction away from the first end and then in an anticlockwise direction, if looking at the lead from its first end.

In a preferred embodiment, the length of the conductive element that is wound in an anticlockwise manner is substantially equal, and preferably is equal, to the length of the conductive element that is wound in a clockwise manner.

At the transition from anticlockwise to clockwise turns, the conductive element is preferably folded back on itself.

In another embodiment, the conductive element continues to be wound in an anticlockwise manner or clockwise manner, when viewed from the first end, for the length of said portion of the insulative body. In this embodiment, the layer is preferably twisted by 180° at a location along the length of the body. In a preferred embodiment, the twist is at about, and preferably exactly at, the midway point of the length of the wound conductive element in the lead.

Each layer of the conductive element is preferably comprised of a plurality of separate electrical conductors. Each layer can have the same number of conductors as the other layers in the element. In another embodiment, the number of conductors of at least one of the layers can vary from the number in one, more or all of the other layers of the element.

According to a third aspect, the present invention is an electrically conducting lead comprising:
a body of relatively electrically insulative material; and
a relatively electrically conductive element extending through at least a portion of said insulative body in a wound arrangement;
wherein said electrically conductive element comprises a plurality of layers of electrical conductors with the number of conductors of at least one of the layers varying from the number of conductors in at least one of the other layers of the element.

In this aspect, the number of conductors in said one of the layers varies from the number in more than one, or all, of the other layers of the element.

In a further embodiment of this aspect, the electrically conductive element extends from a first end to a second end of the lead. In this embodiment, the longitudinal extent of each of said electrical conductors over the length of the lead from the first end to the second end is substantially identical. More preferably, the longitudinal extent of the electrical conductors is identical.

In this aspect, the wound arrangement of the electrically conductive element is preferably a helically wound arrangement. In this regard, the spacing or pitch of the wound arrangement can vary or be identical along said arrangement.

In each of the aspects, the electrical conductors are preferably made of platinum. More preferably, the electrical conductors are made from a sheet of platinum. Each of the leads preferably has a first end that is attachable to or is integrally attached to an electrode pad. Each of the leads further preferably has a second end that is connectable to a stimulator unit that delivers electrical signals through the lead.

In one embodiment of each of the aspects, the lead is preferably implantable in the body of a recipient. In this regard, the materials used to form the lead are preferably suitable for implantation in the body of a recipient.

The electrically insulative body is further preferably formed from a flexible material. Examples of suitable materials include silicone rubber and parylene.

According to a fourth aspect, the present invention is a method of manufacturing a lead according to any one of the preceding aspects, the method comprising the step of:

winding a conductive element relative to and around an insulative body.

In one embodiment, the conductive element can be loaded in a spindle, with one end of the element attached to one end of the insulative body. The insulative body can then be turned in one direction, such as a clockwise direction, causing the conductive element to exit the spindle and become wound around the insulative body. The spindle can be moved longitudinally relative the length of the insulative body.

In one embodiment, the spindle could move in a clockwise direction relatively around the insulative body. If desired, at a mid point along the length of the insulative body, the direction of rotation of the insulative body with respect to the spindle can change to an anticlockwise direction. At this point, the conductive element is caused to fold upon itself such that what was an inner layer of the conductive element becomes the outer layer and vice versa. The conductive element is then wound onto the insulative body in an opposite direction for a length equal to that previously wound onto the insulative body. This results in all layers of the conductive element travelling the same distance and therefore being aligned at both ends of the lead.

Following winding of the conductive element, the insulative body can be coated in another layer of insulative material, such as silicone.

In an alternative method, respective ends of the conductive element can be fixed to respective ends of the insulative body, with the spindle positioned midway between both ends of the insulative body. Once again, the insulative body can be rotated relative to the spindle or the spindle can rotate relative to the insulative body to cause the conductive element to be wound onto the insulative body. As the conductive element is wound onto the insulative body, the spindle moves relatively closer to the insulative body to ensure that the pitch of winding is controlled as desired.

At the mid-point, the winding is complete and the conductive element is removed from the spindle, with all layers of the conducting element travelling the same distance over the length of the insulative body.

In a still further embodiment, the conductive element is again mounted in a spindle with one end of the conductive element connected to one end of the insulative body. When the spindle has wound the conductive element to the mid-point, the spindle is preferably relatively rotated about or exactly 180°. This causes the conductive element to twist such that what was previously the inner layer of the conductive element becomes the outer layer and what was previously the outer layer becomes the inner layer of the conductive element.

Following the formation of the twist in the conductive element, the insulative body is preferably continued to relatively rotate in the same direction to complete the winding.

Use of the methods as defined herein result in the formation of a lead comprising an insulative body having a conductive element wound therein, with preferably, the conductors of the element extending the same length through the lead.

According to a fifth aspect, the present application comprises an electrically conducting lead comprising at least one wire set, each set comprising at least two electrically insulated wires extending across the set in a first direction and disposed substantially in a side-by-side relationship, wherein the set has an undulating form for at least a portion of its length defined by a plurality of ridges and troughs extending across the set in a direction that is at an angle to said first direction.

According to a sixth aspect, the present application comprises a tissue-stimulating prosthesis comprising at least one stimulator means that outputs electrical signals via an electrically conducting lead to an electrode array, the lead comprising at least one wire set connecting the stimulator means to the electrodes of the array, each set comprising at least two electrically insulated wires extending across the set in a first direction and disposed substantially in a side-by-side relationship, wherein the stack has an undulating form for at least a portion of its length defined by a plurality of ridges and troughs extending across the set at an angle to said first direction.

In a preferred embodiment of the fifth and sixth aspects, the ridges and undulations are parallel. Still further, the ridges and undulations are preferably substantially at right angles to said first direction. The peak to peak amplitude of pairs of ridges and troughs is preferably at least substantially constant across the lead. It will, however, be appreciated that the peak to peak amplitude could vary along the length of the lead.

In a further embodiment of the fifth and sixth aspects, the undulating form of the lead is at least substantially sinusoidal. Other waveforms can, however, be envisaged. Still further, the undulating form of the lead extends at least a majority of the length of the lead. In a further embodiment, the undulating form extends the entire length of the lead. In yet a further embodiment, the undulating form extends in separate sections along the lead with each section separated by a length of straight lead.

In a preferred embodiment, each wire comprises a longitudinal portion of a conductive material such as platinum, iridium, or gold encapsulated within a layer of silicone and/or parylene. The conductive material can have a thickness of between about 10 and 50 microns. In each set, the wires are preferably formed in a planar side by side relationship. Still further, the respective wires are substantially parallel.

Each wire preferably extends from a respective single electrode of an electrode array. The electrode array can be formed from a stack of a plurality of sets of electrodes. In one embodiment, the array can comprise 30 electrodes, with the array made up of 5 different sets of electrodes that have been formed individually and then stacked one on top of the other to form a single electrode array. Where the array comprises 30 electrodes, the array can comprise 3 sets of seven electrodes, 1 set of 5 electrodes and 1 set of 4 adjustable electrodes. In this embodiment, the 3 sets of 7 electrodes are stacked one on top of the other, the set of 5 electrodes is stacked on these sets, with the set of 4 electrodes on top of the stack. Other combinations of sets can, however, be envisaged.

While the sets of electrodes are stacked one upon the other, it will be appreciated that the actual position of the electrodes in each set are not necessarily vertically aligned. Rather, the set immediately above its lower set may be laterally offset so as to ensure the electrodes are visible from beneath the stack. The stacks could also be vertically aligned.

In a further embodiment, the electrodes and wires can be formed using electrical discharge machining (EDM), milling, etching or laser cutting.

The wires extending from each electrode are preferably of the same length. It can, however, be envisaged that the wires could be formed with different lengths to account for the ultimate offset present when forming the stack.

In a further embodiment of the fifth and sixth aspects, the lead can further comprise an outer layer encapsulating at least said portion of the lead that has the undulating form. The outer layer can be substantially rectangular in cross-section. In another embodiment, the outer layer can be tubular with said undulating portion disposed in a lumen of the tube.

In a further embodiment, the undulation in the lead is formed by passing the lead between at least two wheel or rollers having interengaging teeth. The shape, size and spacing of the teeth is adapted to result in the desired undulating form in the lead. It will be appreciated that the undulating form can be changed by making appropriate changes to the wheels or rollers or using alternative wheels or rollers as required.

The presence of the undulating form in the lead improves the flexibility of the lead and allows it to compensate for any movement between the stimulating means and the electrode array. This serves to minimise force on feedthroughs used to connect the wires to the stimulator means.

In a preferred embodiment, the tissue-stimulating prosthesis can comprise a cochlear implant system.

BRIEF DESCRIPTION OF THE DRAWINGS

By way of example only, preferred embodiments of the invention are now described with reference to the accompanying drawings, in which:

FIG. 6 is a view of one embodiment of the conductive lead according to the present invention;

FIGS. 7a and 7b are end views of the conductive element of FIG. 6;

FIG. 8 is a side view of one end of the conductive element of FIG. 7a; and

FIG. 9 is a view of another embodiment of the conductive lead of the present invention;

FIG. 10 is a view of yet another embodiment of the conductive lead of the present invention;

PREFERRED MODE FOR CARRYING OUT THE INVENTION

Figure 1:
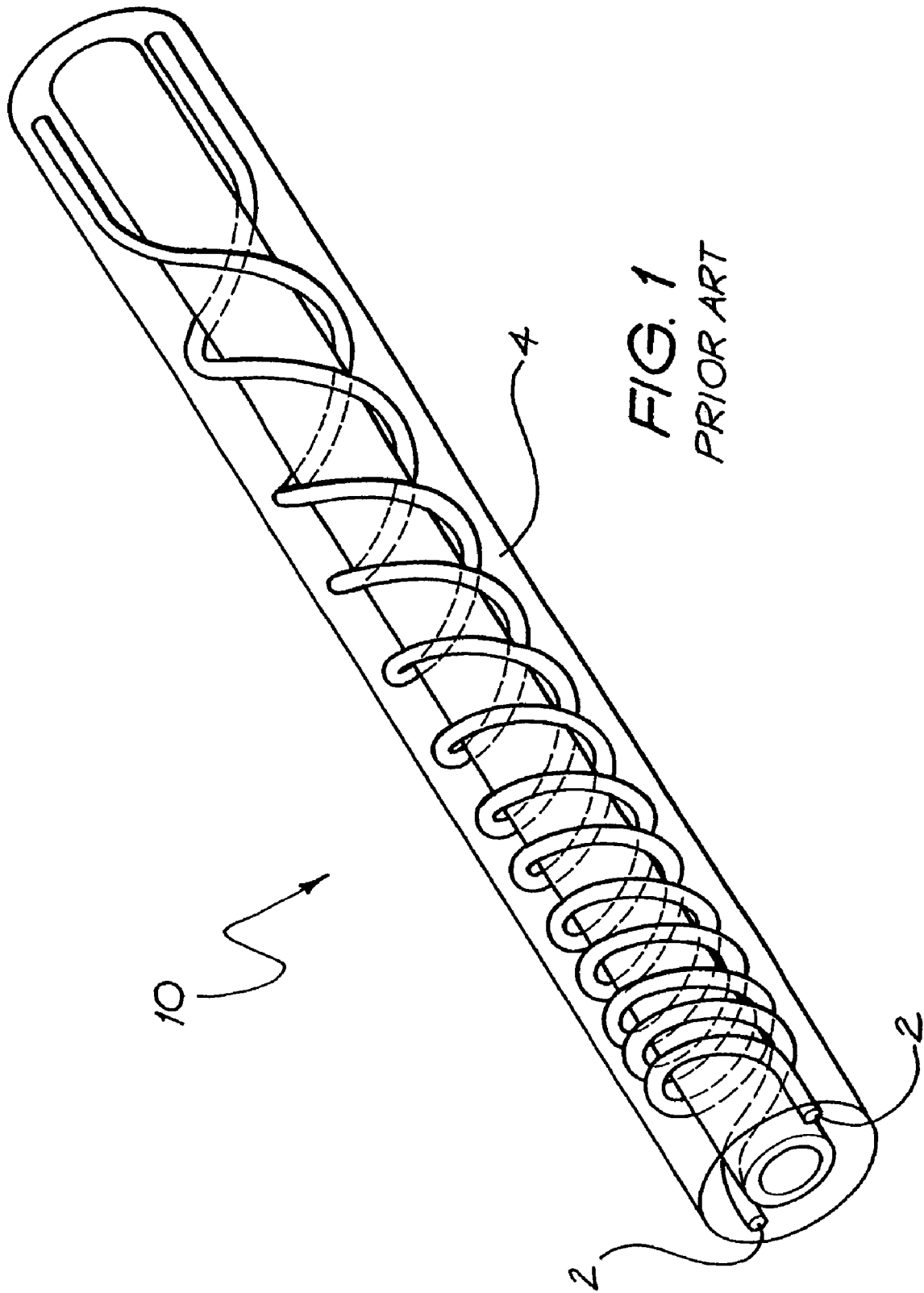
FIG. 1 is a perspective view of a prior art lead used in implantable devices.

FIG. 1 depicts generally as 10 one example of a conventional conducting lead that is used in implantable medical devices. This lead 10 has a plurality of conducting wires 2 extending therethrough. Each of these wires 2 can be connected at one end to a stimulator unit and at the other end to a stimulating/sensing electrode so that an electric signal can be transmitted from the stimulator unit to the corresponding electrode. The wires 2 are typically embedded in a body-compatible material 4, such as polyurethane, an organo-silicon polymer, or any other suitable non-conductive plastic.

Typically, the body-compatible material 4 can undergo some degree of extension or flex. As shown, each of the wires 2 are arranged within the body compatible material 4 in a helical manner to ensure that the lead 10 can extend without placing undue stress on the wires 2. As is shown, the pitch of the wire helix can also be altered to vary the flexibility of the conducting lead 10 along its length.

Figure 2:
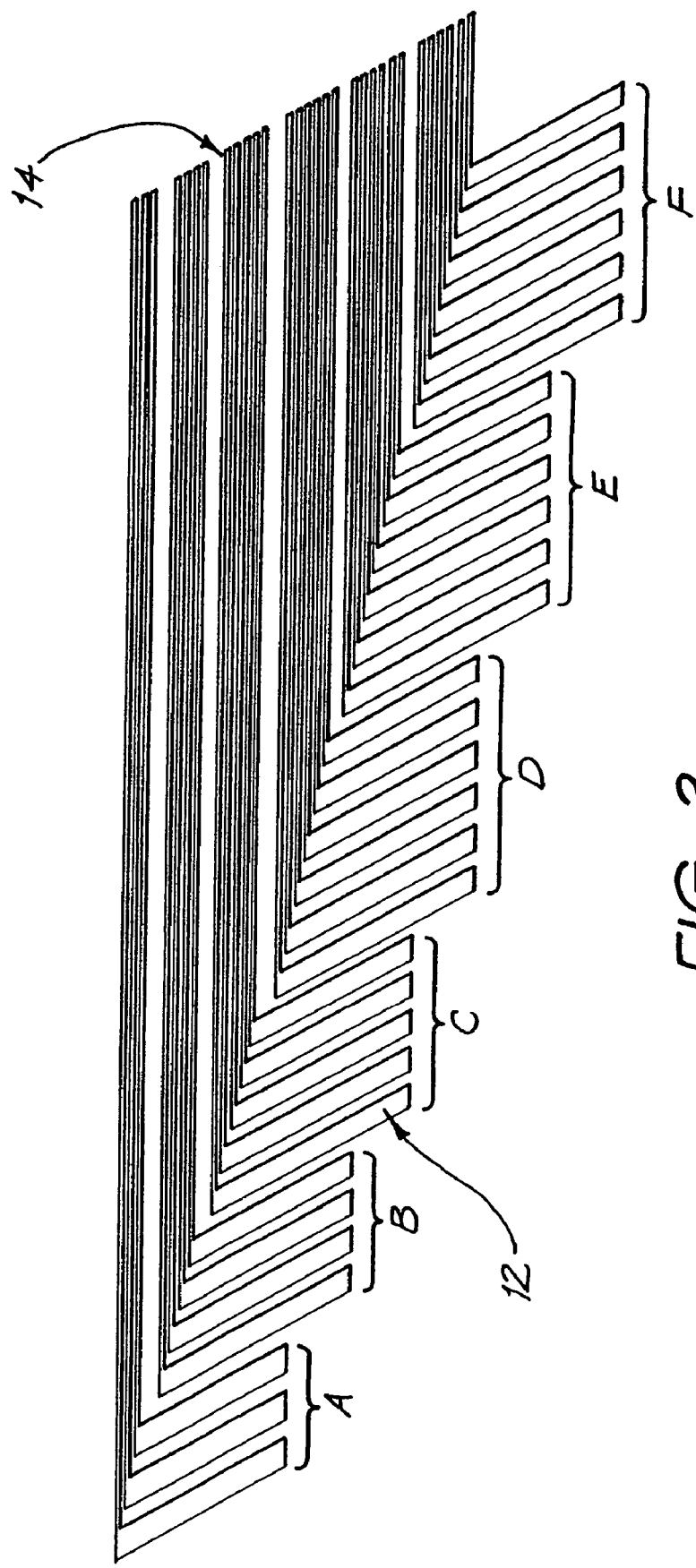
FIG. 2 is a view of electrode pads and conducting portions according to one embodiment of the present invention.
Figure 3:
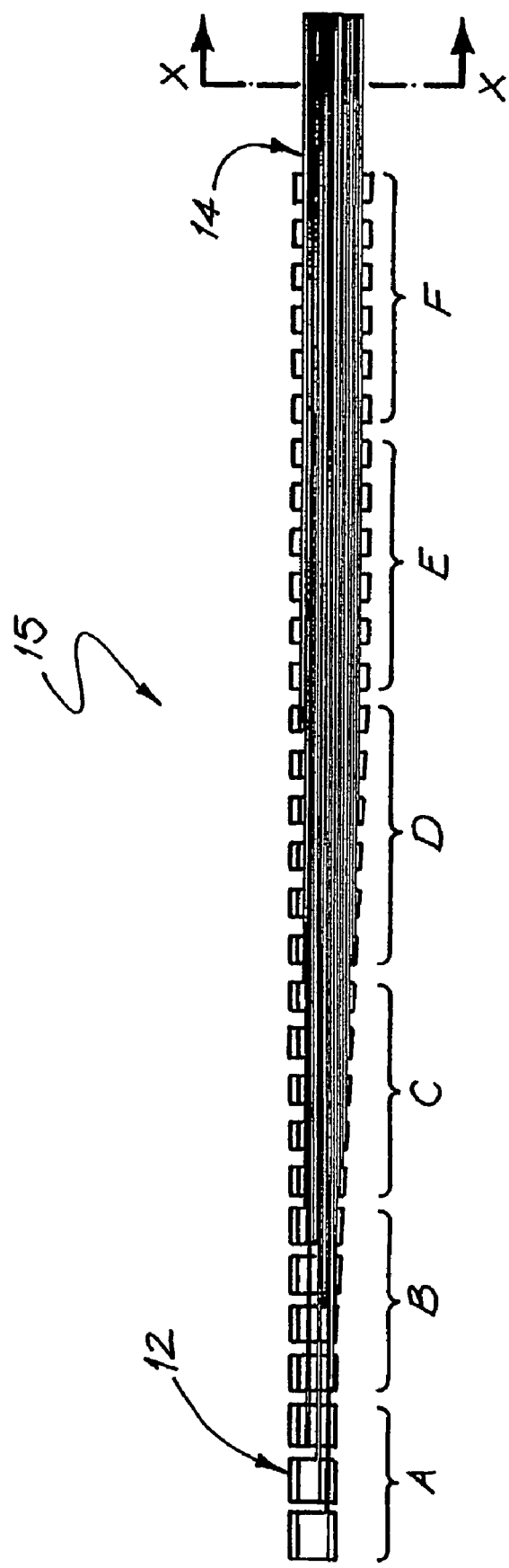
FIG. 3 is a top view of an electrode array arrangement.

FIGS. 2 and 3 depict one arrangement of stimulating electrode pads and leads for use in the present invention. This particular arrangement is described in more detail in International Patent Application No. PCT/AU02/00575, the contents of which is incorporated herein by reference. In this application, the present invention is described in relation to a cochlear implant application, however it will be appreciated that the present invention is also applicable to other applications that employ a conducting lead to deliver electrical signals or pulses.

FIG. 2 depicts the electrode pads 12 and conducting portions 14 (i.e. the electrically conducting leads for each electrode pad 12) as being formed in a series of groups that are herein labelled as groups A-F. As is clearly evident, the electrode pads 12 and the conducting portions or wires 14 are formed as one piece. In the depicted embodiment, they are formed from a sheet of suitable conductive material, such as platinum, in accordance with the methods described in Application No. PCT/AU02/00575. The electrode pads 12 and wires 14 are made from a sheet of platinum or similar conducting material, and covered in a coating of electrically insulating material such as silicone rubber or a polymer material such as parylene.

The electrode pads 12 are then shaped accordingly to suit the application. In the depicted embodiment, the pads 12 are shaped into a U-shape, with the wires 14 running centrally from the electrode pads 12 (see FIG. 3). In this example, each of the electrode array groups A-F are formed separately, but preferably from a single sheet of platinum, thereby forming a series of electrode arrays, with each array consisting of a plurality of electrode pads 12 with centrally positioned wires 14 connected thereto.

Each of the electrode array groups A-F can be arranged longitudinally, to form a multi-electrode array structure 15. Such an array can then be used, for example, as a cochlear implant electrode array. In the embodiment shown, electrode array group A is stacked and positioned on top of electrode array group B which is then stacked and positioned on top of electrode array group C, and so on. This arrangement produces an electrode array structure that is shown more clearly from the top view of the structure provided as FIG. 3.

In the embodiment shown in FIG. 3, the electrode array structure 15 consists of 30 individual electrode pads 12, with each electrode pad 12 having an integral conducting portion or wire 14 extending therefrom and running centrally along the electrode array structure 15. Following the formation of the electrode array structure 15, the array can be moulded in a suitable bio-compatible material 41 such as silicone and shaped accordingly, as is known in the art and which is not essential to an understanding of the present invention.

In the embodiment described, the electrode array structure is shown consisting of 30 individual electrode pads 12, however it should be appreciated that the electrode array structure could consist of any number of electrode pads and still be applicable to the present invention.

Figure 4:
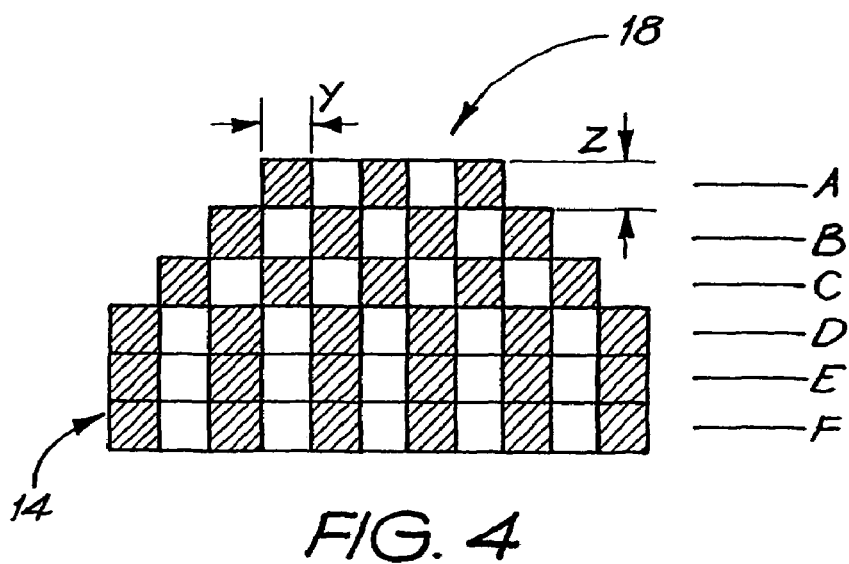
FIG. 4 is a cross sectional view of the conductive element of FIG. 3 along X-X.

In an electrode array constructed in the manner shown in FIGS. 2 and 3, the conducting portions 14 resulting from such an arrangement will be formed in the manner shown in FIG. 4. In this regard, FIG. 4 can be considered a cross-section of the conducting portions 14 of FIG. 3 along line X-X. As is clearly evident, the conducting portions 14 associated with each of the electrode array groups A-F are arranged in a layered format, with the most distant electrode array group A being the top layer, and the most proximal electrode array group F being the bottom layer, this layered format being generally referred to as the conducting element 18.

Figure 5:
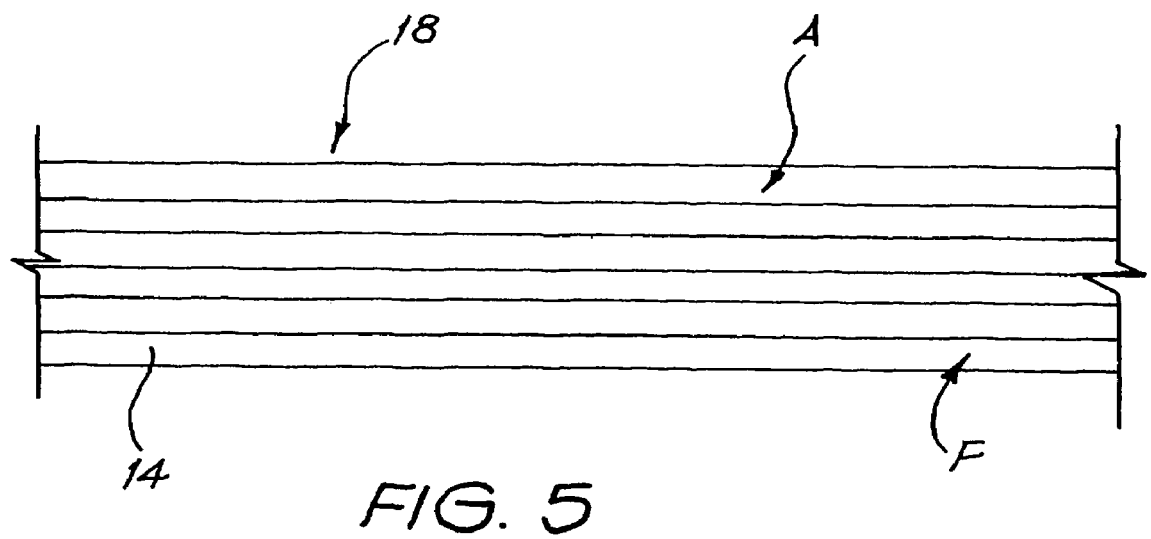
FIG. 5 is a side view of the conductive element of FIG. 4.

This conducting element 18 is more clearly shown in FIG. 5, which is a side view of the conducting element 18 shown in FIG. 4. From these figures, it is evident that the resulting format of the conducting element 18 has a layered, ribbon-like format with each of the conducting portions 14 connected to an integral electrode pad 12 at one end and connectable to a stimulator unit at the other end via a suitable feedthrough device. It is also to be understood in looking at FIG. 4 that each of the conducting portions 14 are electrically insulated from all of the other conducting portions in the element 18.

In the embodiment shown in FIG. 4, the conducting element 18 is made up of six layers (A-F) however the number of layers is dependant upon the design of the electrodes and as such any number of layers could be used as desired. Also, FIG. 4 depicts the conducting element 18 being made up of layers having different numbers of conducting portions 14, for example layer A is depicted as having 3 conducting portions, layer B with 4, layer C with 5 and layers D-F with 6 conducting portions. It should be appreciated that the number of conducting portions 14 provided in each of the layers is not critical to the present invention as the layers could all contain the same number of conducting portions or all contain different numbers and still fall within the scope of the present invention.

In the embodiment shown in FIG. 4, each of the conducting portions 14 are shown having a substantially square cross-sectional area. It should be appreciated however that the conducting portions could be of any cross sectional shape. The dimensions of the conducting portions 14 shown also vary dependant upon the desired application. Possible dimensions of the conducting portions may have a width Y of between about 5-50 μm and a thickness Z of between about 10-100 μm. In the depicted embodiment, the width Y of the conducing portions is 25 μm and the thickness Z is 15 μm.

As the conducting portions 14 together form a layered, ribbon-like conducting element 18, each of the portions 14 cannot easily be separated and individually coiled to form a helical conducting lead as is typical in the prior art and shown in FIG. 1. Instead, it is desirable to form a connecting lead wherein the conducting element 18 is maintained in a layered, ribbon format within a coating of insulative and biocompatible material, such as a silicone or parylene.

Therefore the formation of such a lead that is capable of providing adequate flexibility and elongation as well as being bio-compatible and insulative is important in providing a safe and effective connection between an implantable stimulator unit and stimulating electrodes.

FIG. 6 depicts one embodiment of a conducting lead according to the present invention. In this embodiment, the lead 20 includes a conducting element 18 helically wound within a body of insulative material having good body compatibility, such as a silicone or parylene. As is depicted, the conducting element 18, which is shown in cross-section detail in FIGS. 7a and 7b, is made up of a plurality of layers with each layer consisting of a plurality of conducting portions 14. The pitch of the helix is controlled so that the flexibility of the lead 20 can be altered as desired. One end of the lead 20 is preferably connected to a stimulator unit, whilst the other end of the lead may be connected to stimulating electrodes, such as those shown in FIGS. 2 and 3.

FIGS. 7a and 7b show cross-sectional views of the conducting element 18 at each end of the lead 20. As shown in FIG. 7a, the conducting element 18 may consist of a plurality of layers of conducting portions 14 with each layer having the same number of conducting portions 14. It will be appreciated that the conducting element may be as is depicted in FIG. 4, with some of the layers having different numbers of conducting portions 14.

In this embodiment, by providing a layered conducting element 18 the position of the conducting portions 14 with respect to each other can be maintained throughout the length of the lead 20. As is shown in FIGS. 7a and 7b, conducting portion A1 can be easily identifiable at both ends of the lead 20 allowing for easy determination and connection of the electrode to the appropriate contact. In prior art devices whereby individual or bunched wires are helically wound within an insulative material (as depicted in FIG. 1), such direct identification is not easily provided for. Providing such easy identification of the conducting portions 14 allows for considerable time reductions in the manufacture of such devices. Without this, the task of connecting the lead to the stimulator is particularly arduous, as each connecting portion must be individually tested to determine the electrode pad 12 to which it is connected. This time saving aspect becomes particularly important when the number of electrode pads 12 is increased, requiring much sorting of the conducting portions 14 prior to connection to the stimulator unit.

In the embodiment depicted in FIG. 6, each of the layers of the conducting element 18 are not aligned at both ends. The result of this is depicted in FIG. 8, which shows one end of the conducting element 18 of the present invention. This difference in alignment is because the outer layer (A) of the conducting element 18 will travel a greater distance in the helix than the inner layer (F) of the conducting element 18. In some instances, the alignment of each of the conducting portions 14 at both ends will not be critical, as the conducting portions may be separately connected to the stimulator unit using an appropriate feedthrough device.

FIGS. 9 and 10 depict embodiments of the present invention similar to the embodiment shown in FIG. 6, but which provide for alignment of the conducting portions 14 at both ends of the lead 20.

In the embodiment shown in FIG. 9, the conducting element 18 is helically wound in one direction, eg anti-clockwise, for a portion of the length of the lead 20, and then helically wound in an opposite direction, eg clockwise, for another portion of the length of the lead 20. In this regard, it is preferred that the conducting element 18 is wound such that each layer travels the same distance over the length of the lead, providing alignment of the conducting portions at both ends. This can be achieved by winding the conducting element 18 in one direction for half the length of the lead 20 and at a midpoint 22, winding the conducting element 18 in the opposite direction for the remaining half of the lead. Alternatively, the conducting element 18 may be wound in alternative directions for a number of cycles over the length of the lead, ensuring that the cycles of both the clockwise and anticlockwise windings are identical over the length of the lead 20.

By controlling the point 22 at which the winding of the conducting element 18 changes from clockwise to anti-clockwise, each layer of conducting portions 14 of the conducting element 18 can be wound so that they each travel the same distance over the length of the lead 20. In the embodiment shown in FIG. 9, the point 22 where the winding changes direction, is achieved by folding the conducting element back upon itself thereby causing the inside layer 31$i$ (the cross-hatched side) to become the outside layer 31$o$ and what was previously the outside layer 32$o$ becomes the inside layer 32$i$.

In the embodiment depicted in FIG. 10, an alternative method of achieving this alignment is shown wherein the conducting element 18 is twisted by 180 degrees causing what was previously the inside layer 31$i$ to become the outside layer 31$o$ and what was previously the outside layer 32$o$ to become the inside layer 32$i$. In this method, the direction of winding does not have to be changed and by controlling the number of turns and the pitch of the winding, the distance travelled by each layer of the conducting element 18 over the desired length of the lead 20 is controlled.

Figure 11A:
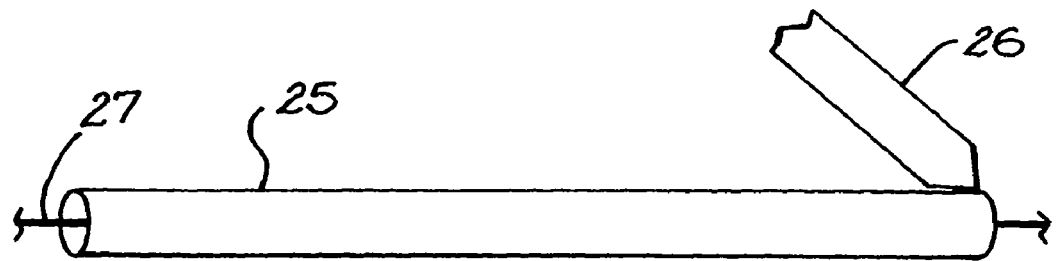
FIGS. 11a-11c depict the steps associated with one method of constructing the conductive lead as shown in FIG. 9.
Figure 11B:
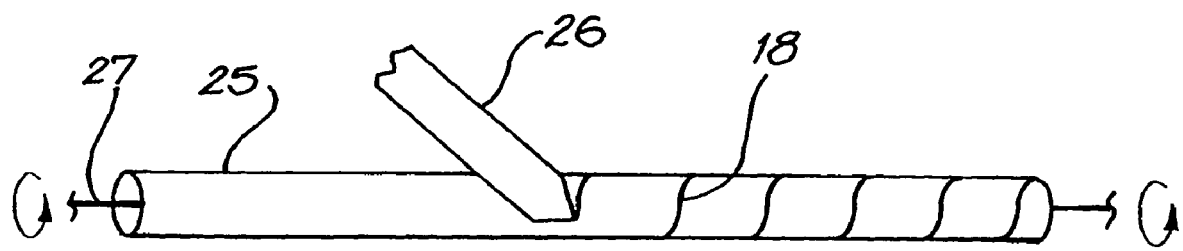
Figure 11C:
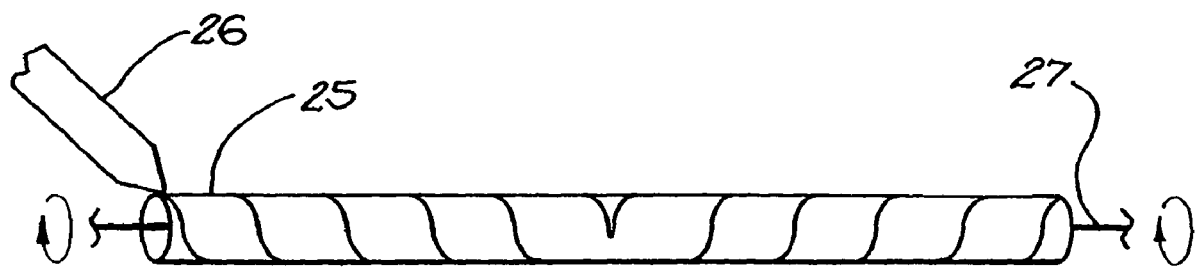

A lead 20, such as that shown in FIG. 9 can be manufactured in the manner depicted in FIGS. 11$a$-11$c$. In FIG. 11$a$, a silicone tube 25 is shown placed over a mandrel 27 extending through the silicone tube 25 and supported at both ends by chucks (not shown). A spindle 26 is then loaded with the conducting element 18 for winding onto the silicone tube 25. As shown in FIG. 11$a$, the conducting element 18 is first fixed at one end of the silicone tube 25 prior to winding.

As shown in FIG. 11$b$, the chucks supporting the mandrel 27 are then turned in one direction, eg a clockwise direction, and the conducting element 18 is caused to exit the spindle 26 and become wound around the silicone tube 25. The spindle 26 can move longitudinally along the length of the silicone tube 25 as it rotates. It will be appreciated that the tube 25 could also be moved longitudinally relative to a stationary or moving spindle 26.

In one embodiment, the spindle 26 could move in a clockwise direction around the silicone tube 25. At a mid point, shown in FIG. 11$b$, the direction of rotation of the silicone tube with respect to the spindle 26 can change. At this point the conducting element 18 is then folded upon itself, as described in relation to FIG. 9, such that the inside layer becomes the outside layer and vice versa.

As shown in FIG. 11$c$, the direction of rotation of the silicone tube 25 then changes from clockwise to anti-clockwise, and the conducting element 18 is then wound onto the silicone tube 25 in an opposite direction. This results in all layers of the conducting element 18 travelling the same distance and therefore being aligned at both ends of the lead. Following winding of the conducting element 18, the silicone tube 25 and mandrel 27 can be removed from the chucks and coated in another layer of insulative material, such as silicone. The mandrel 27 can then be removed from the silicone tube 25 and further insulative material such as silicone can then be injected into the space left by the mandrel 27 to form a lead 20 as shown in FIG. 9.

Figure 12A:
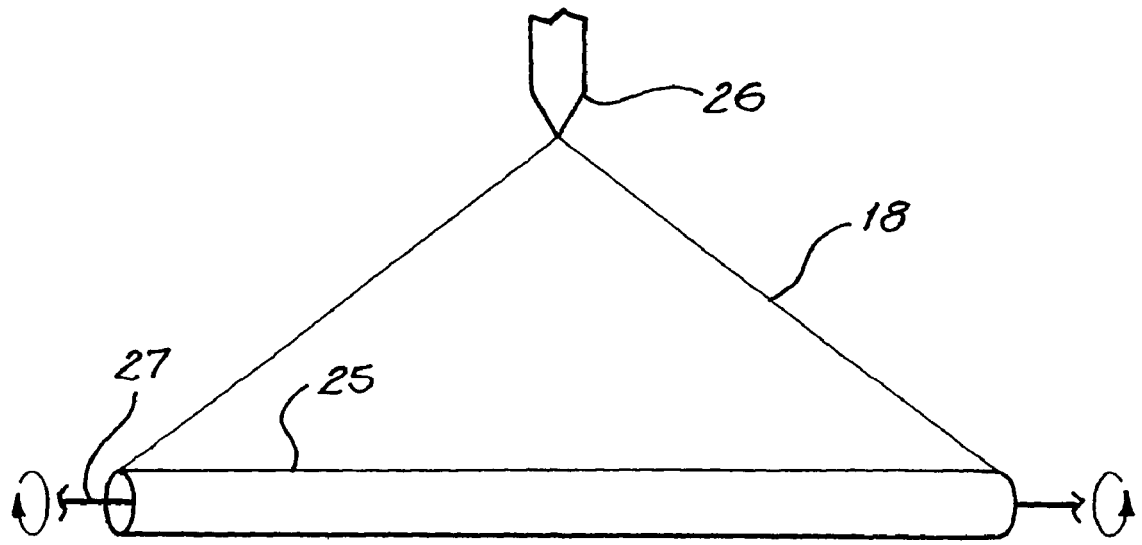
FIGS. 12a-12c depict the steps associated with another method of constructing the conductive lead as shown in FIG. 9.
Figure 12B:
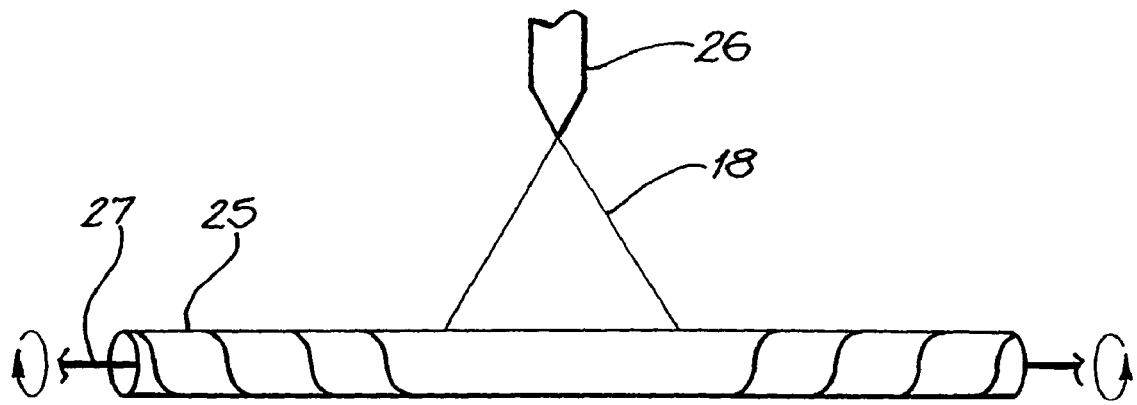
Figure 12C:
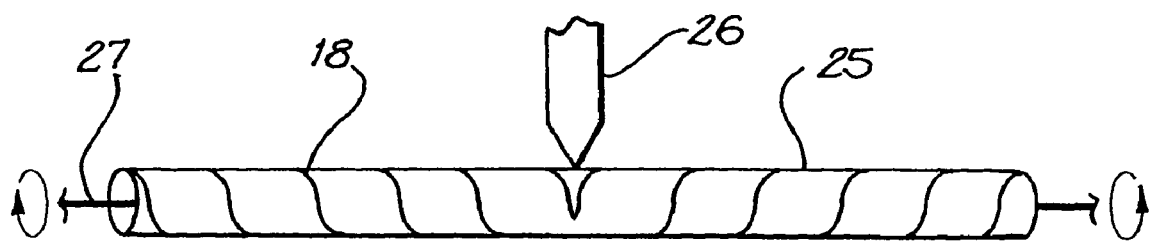

An alternative method of manufacturing the lead of FIG. 9 is depicted in FIGS. 12$a$-12$c$. In this method the conducting element 18 is fixed at both ends to the silicone tube 25, and the spindle 26 is positioned midway between both ends of the silicone tube 25, as shown. Once again, the silicone tube 25 can be rotated relative to the spindle 26 or the spindle 26 can rotate relative to the silicone tube 25 to cause the conducting element 18 to be wound onto the silicone tube 25. As the conducting element 18 is wound onto the silicone tube 25, the spindle moves relatively closer to the silicone tube 25 to ensure that the pitch of winding is controlled as desired.

At the mid-point, as shown in FIG. 12$c$, the winding is complete and the conducting element 18 is removed from the spindle, with all layers of the conducting element travelling the same distance over the length of the silicone tube 25, producing a lead 20 as shown in FIG. 9.

Figure 13A:
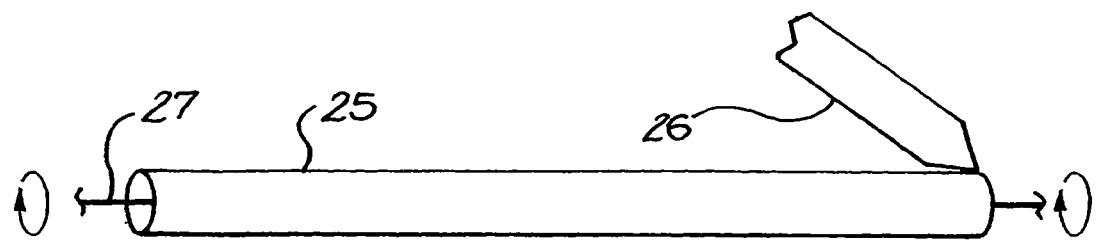
FIGS. 13a-13c depict the steps associated with a still further method embodiment of constructing the conductive lead as shown in FIG. 10.
Figure 13B:
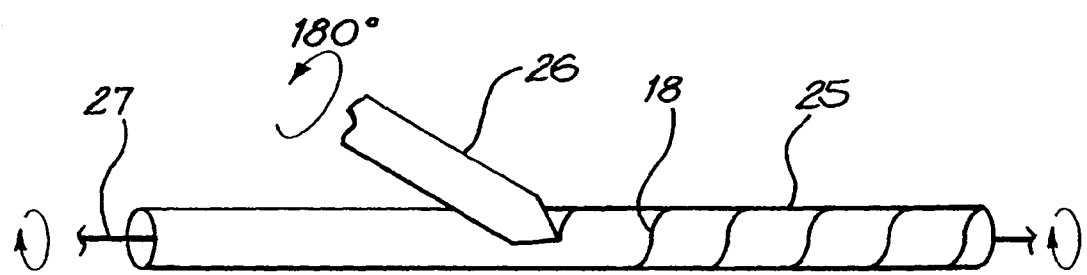
Figure 13C:
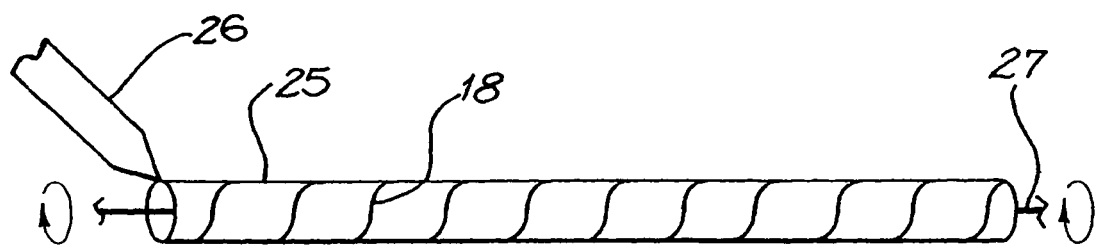

A lead 20, such as that shown in FIG. 10 can be manufactured in the manner shown in FIGS. 13$a$-13$c$. In FIG. 13$a$, the same arrangement as that described in relation to FIG. 11$a$ is used. However, in this embodiment, when the spindle 26 has wound the conducting element 18 to the mid-point, as shown in FIG. 13$b$, the spindle 26 is rotated 180 degrees, as shown. In this regard, the conducting element 18 is "twisted" such that what was previously the inner layer of the conducting element 18 becomes the outer layer and what was previously the outer layer becomes the inner layer of the conducting element 18. This is shown in more detail in FIG. 10.

Following this "twist", the silicone tube 25 and mandrel 27 arrangement is rotated in the same direction and the winding is completed. In this regard, a lead similar to or the same as that shown in FIG. 10 is created with the winding occurring in one direction similar to that shown in FIG. 6.

Whilst the above three embodiment describe a silicone tube 25 forming the winding surface, it should be appreciated that other such materials could be used to create such a lead. Other such materials could be parylene or any other material that is both insulative and flexible and which is also body-compatible.

Figure 14:
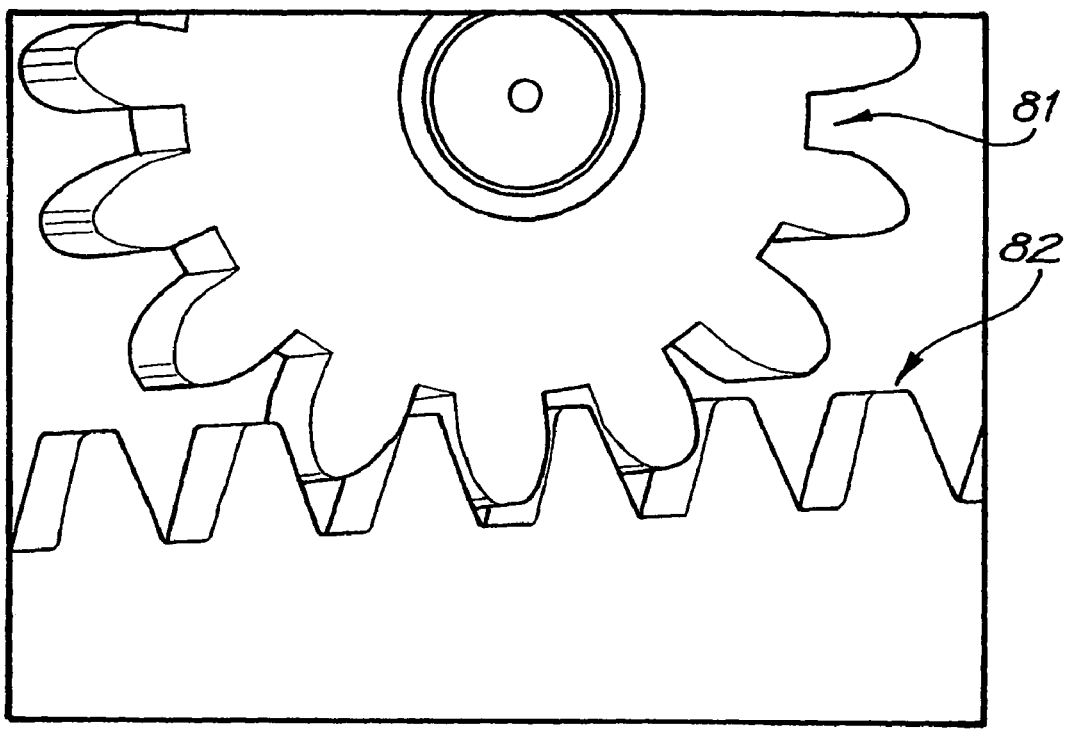
FIG. 14 depicts a pair of gear wheels for forming an undulation in at least a portion of the lead.
Figure 15A:
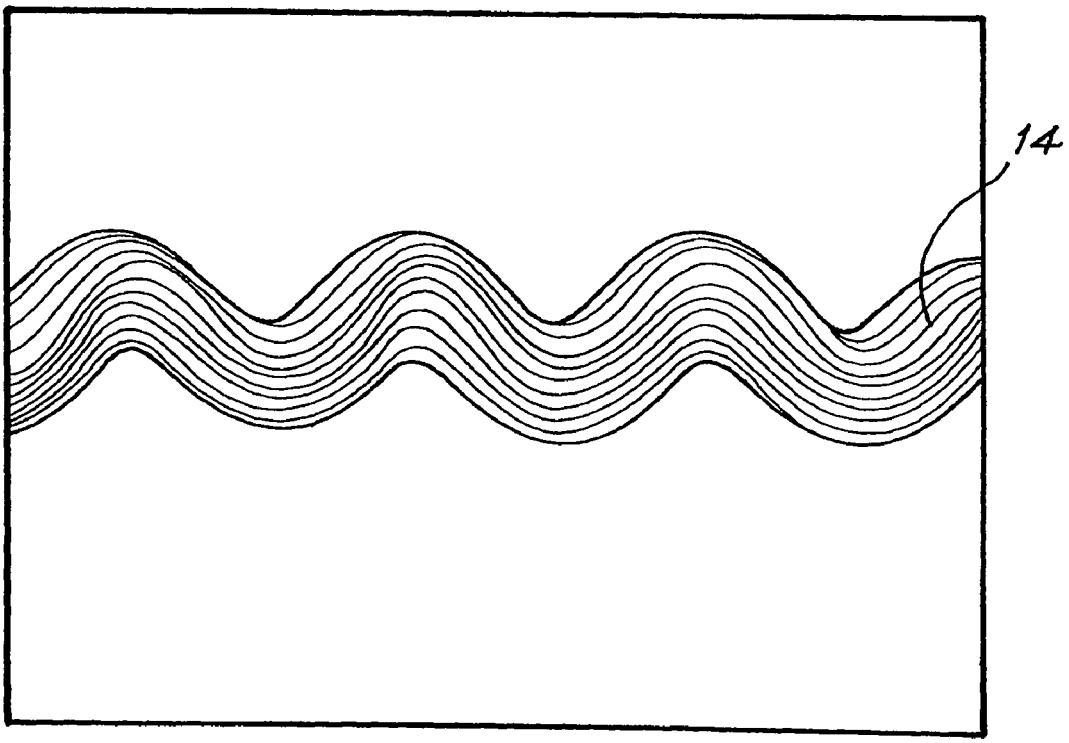
FIGS. 15a-15c depict an undulating lead formed using the gear wheels of FIG. 14.
Figure 15B:
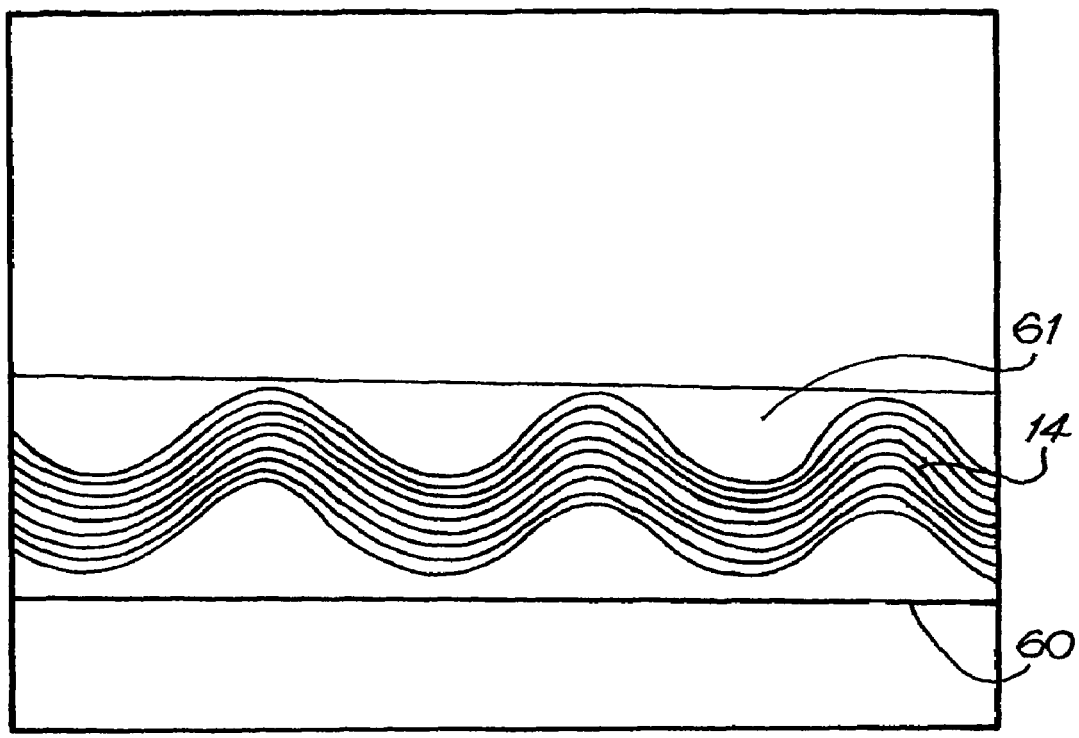
Figure 15C:
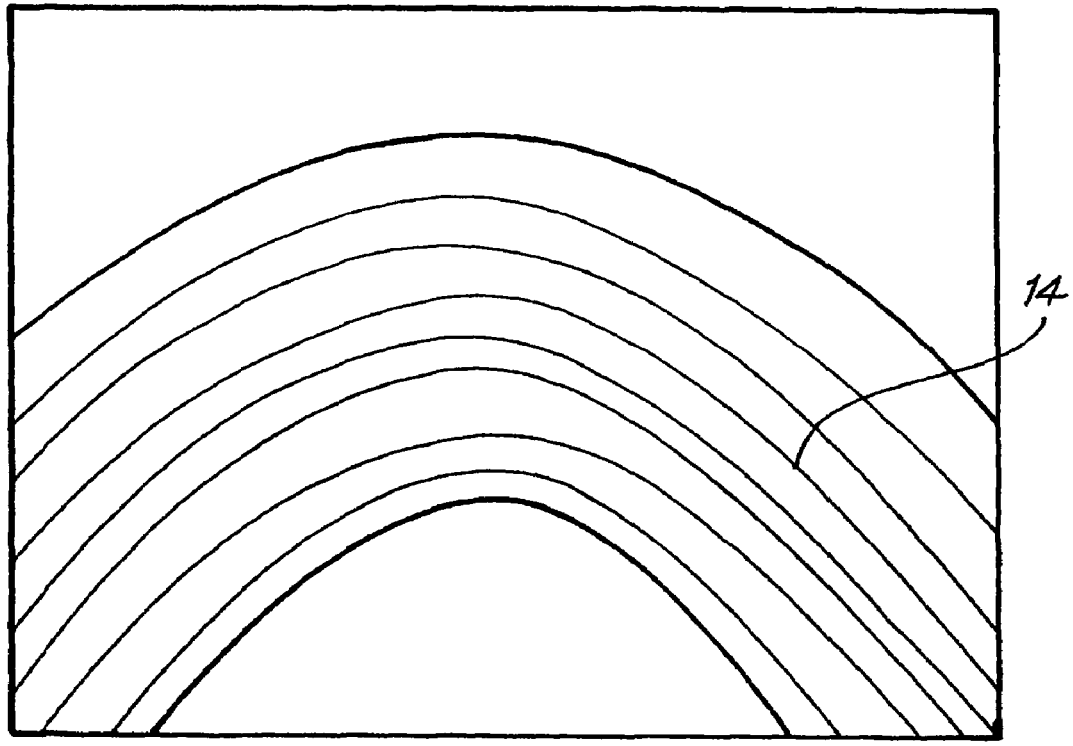

Another lead arrangement is depicted in FIGS. 15$a$ to 16$b$. Here, the plurality of stacked sets of conducting portions or wires 14 act together to form a lead 60 that is adapted to extend from a stimulator, such as the stimulator of a cochlear implant, to the electrodes 12. Once the lead 60 is formed, at least a portion of it distal from the electrodes 12 can be passed through a set of toothed wheels 81,82 or the like, such as is depicted in FIG. 14. The teeth of the wheels 81,82 serve to form an undulating form in the lead 60 as is depicted in FIGS. 15$a$-15$c$.

As depicted, the undulating form is substantially sinusoidal with the peak to peak amplitude of the undulating form substantially constant along its length. If desired, at least the undulating portion of the lead can be encapsulated within a silicone and/or parylene tube or outer layer 61, as is depicted in FIG. 15$b$.

Figure 16A:
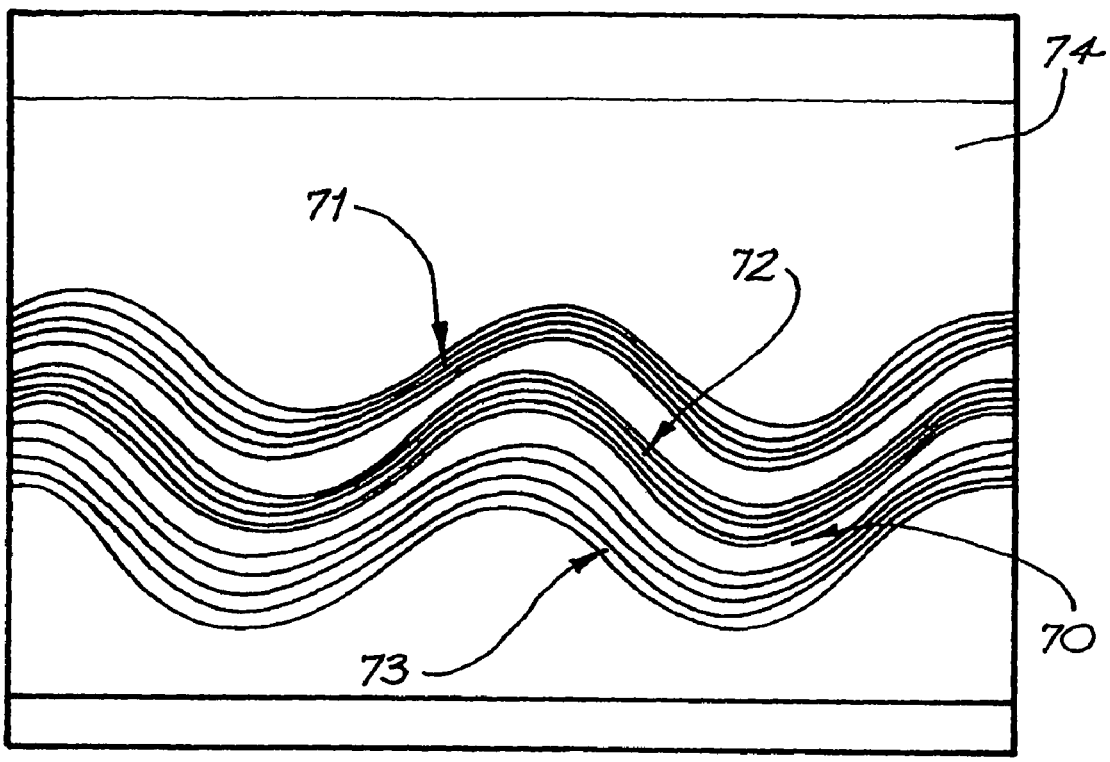
FIGS. 16a-16b are photos depicting another embodiment of an undulating lead according to the present invention.
Figure 16B:
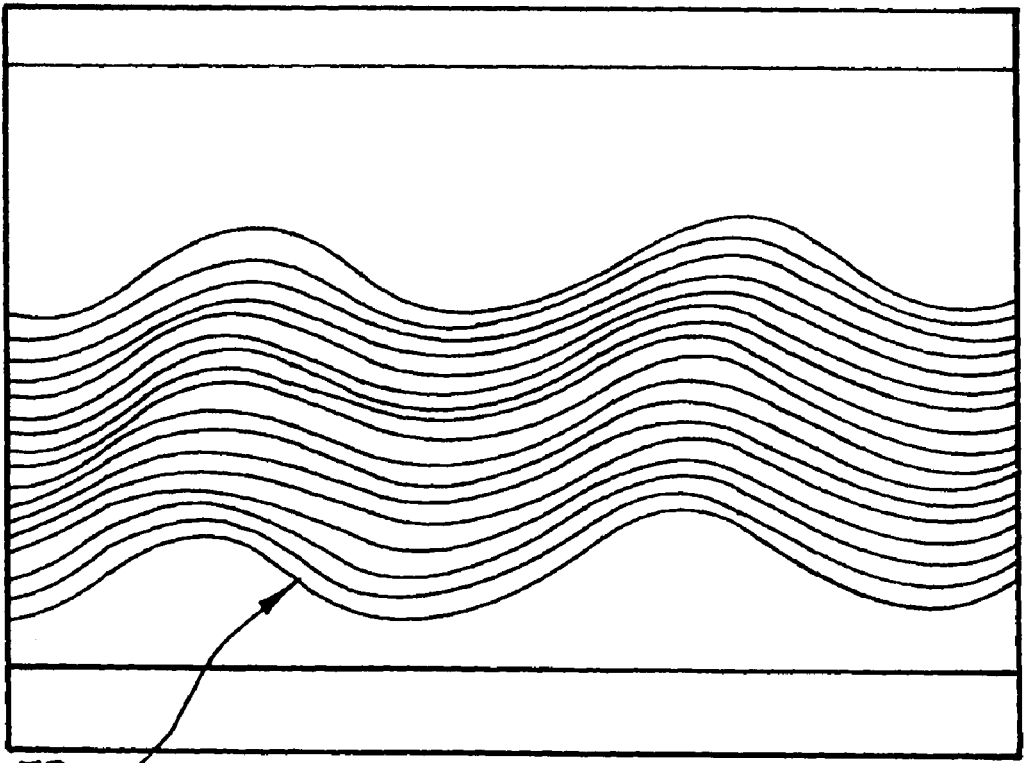

FIGS. 16$a$ and 16$b$ depict an embodiment wherein a stack of a plurality of sets of wires 14 have passed through the wheels 81,82 to form an undulating lead 70 according to the present invention. In this embodiment, the lead comprises three sets (71,72,73) of wires 42 stacked one on the other. The undulating portion of the lead has then been encapsulated in an outer tube 74. Substantially flat-form cables and cables of rectangular or other cross-sections can also be envisaged.

The presence of the undulating form in the lead 70 improves the flexibility of the lead 70 and allows it to compensate for any movement between the stimulator and the electrodes 12 of the array. This serves to minimise force on feedthroughs used to connect the wires 14 to the stimulator.

The present invention therefore maintains the layered nature of the conducting element and provides a conducting lead that ensures easy identification of the conducting portions and their associated stimulating pads. The present invention also provides for a flexible and coiled lead that aligns each of the layers of the conductor at either end of the lead.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An electrically conducting lead comprising:
   an electrically-insulative elongate body; and
   an electrically conductive element, wound in an anticlockwise direction for a first length of said body and in a clockwise direction for a second length of said body, having first and second ends and comprising a plurality of layers, each said layer comprising a plurality of electrical conductors positioned within said conductive element such that a first length of each conductor is wound around said body in an anticlockwise direction and a second length of each conductor is wound around said body in a clockwise direction,
   wherein first ends of each of said conductors at said first end of said conductive element are correspondingly identifiable at said second end of said conductive element as second ends of each of said conductors, based on the corresponding position within said conductive element of each of said first and second ends of said conductors with respect to the positions of the other conductors.

2. The electrically conducting lead of claim 1 wherein the wound arrangement of the electrically conductive element is a helically wound arrangement.

3. The electrically conducting lead of claim 1 wherein said electrically conductive element extends from a first end to a second end of said lead.

4. The electrically conducting lead of claim 3 wherein the longitudinal extent of each of said plurality of electrical conductors over the length of said lead from said first end to said second end is substantially identical.

5. The electrically conducting lead of claim 4 wherein the longitudinal extent of each of said plurality of electrical conductors over the length of said lead from said first end to said second end is identical.

6. The electrically conducting lead of claim 1 wherein the length of said conductive element that is wound in an anticlockwise manner is equal to the length of said conductive element that is wound in a clockwise manner.

7. The electrically conducting lead of claim 6 wherein at the transition from anticlockwise to clockwise windings, said conductive element is folded back on itself.

8. The electrically conducting lead of claim 1 wherein each of said plurality of layers of said conductive element is comprised of a plurality of separate electrical conductors, with each of said plurality of layers having the same number of conductors as the other layers in said conductive element.

9. The electrically conducting lead of claim 1 wherein each of said plurality of layers of said conductive element is comprised of a plurality of separate electrical conductors, with the number of conductors of at least one of the of said plurality of layers varying from the number in one, more or all of the other layers of said conductive element.

10. The electrically conducting lead of claim 1 wherein the electrical conductors are made of platinum.

11. An electrically conducting lead comprising:
    an electrically-insulative elongate body; and
    an electrically conductive element, wound in an anticlockwise direction for a first length of said body and in a clockwise direction for a second length of said body, having first and second ends and comprising a plurality of layers, each said layer comprising a plurality of electrical conductors positioned within said conductive element such that the plurality of electrical conductors are wound in an anticlockwise direction around said body for a first length, and in a clockwise direction around said body for a second length,
    wherein said plurality of electrical conductors of at least one of the layers varies in number from the number of said plurality of electrical conductors in at least one of the other of said plurality of layers, and
    wherein said plurality of electrical conductors are positioned within said conductive element such that first ends of each of said conductors at the at said first end of said conductive element are correspondingly identifiable at said second end of said conductive element as second ends of each of said conductors, based on the corresponding position within said conductive element of each of said first and second ends of said conductors with respect to the positions of the other conductors.

12. The electrically conducting lead of claim 11 wherein the number of conductors in said one of the layers varies from the number in more than one of the other layers of the element.

13. An electrically conducting lead comprising:
    an electrically-insulative elongate body; and
    an electrically conductive element, helically wound in an anticlockwise direction for a first length of said body and in a clockwise direction for a second length of said body, having first and second ends and comprising a plurality of layers, each said layer comprising a plurality of electrical conductors positioned within said conductive element such that the position of each of said plurality of electrical conductors comprising each layer with respect to said plurality of electrical conductors of neighboring layers remain constant between said first and said second ends of said insulative body,
    wherein each of said plurality of electrical conductors are positioned such that each conductor is wound in an anticlockwise direction around said body for a first length and in a clockwise direction around said body for a second length, and wherein first ends of each of said conductors at the first said first end of said conductive element are correspondingly identifiable at said second end of said conductive element as second ends of each of said conductors, based on the corresponding position within said conductive element of each of said first and second ends of said with respect to the positions of the other conductors.

14. The electrically conducting lead of claim 1 wherein with the longitudinal extent of each of said electrical conductors over said portion of the lead are substantially identical when in said wound arrangement.

* * * * *